(12) United States Patent
Tam et al.

(10) Patent No.: US 6,472,532 B1
(45) Date of Patent: Oct. 29, 2002

(54) PROCESSES FOR THE MANUFACTURING OF 3-HYDROXY-N,1,6-TRIALKYL-4-OXO-1,4-DIHYDROPYRIDINE-2-CARBOXAMIDE

(75) Inventors: Tim F. Tam, Woodbridge (CA); Wanren Li, Etobicoke (CA)

(73) Assignee: Apotex, Inc., Ontario (CA)

(*) Notice: Subject to any disclaimer, the term of this patent is extended or adjusted under 35 U.S.C. 154(b) by 0 days.

(21) Appl. No.: 10/100,133

(22) Filed: Mar. 19, 2002

Related U.S. Application Data

(62) Division of application No. 09/985,269, filed on Nov. 2, 2001.

(51) Int. Cl.[7] .................................................. C07D 211/86
(52) U.S. Cl. ........................................................ 546/296
(58) Field of Search ......................................... 546/296

(56) References Cited

U.S. PATENT DOCUMENTS

| | | |
|---|---|---|
| 4,840,958 A | 6/1989 | Hider et al. |
| 5,480,894 A | 1/1996 | Hider et al. |
| 5,688,815 A | 11/1997 | Zbinden |

FOREIGN PATENT DOCUMENTS

| | | |
|---|---|---|
| FR | 1516463 | 3/1968 |
| WO | WO 98/54138 | 12/1998 |

OTHER PUBLICATIONS

Liu et al, Synthesis, Physicochemical Characterization, and Biological Evaluation of 2–(1′–Hydoxyalkyl)–3–hydroxypyridin–4–ones: Novel Iron Chelators with Enhanced pFe$^{3+}$ Values, *J. Med. Chem.*, 42 (23), 4814–4823, 1999.

Ellis et al, "Synthesis, Physicochemical Properties, and Biological Evaluation of Hydroxypyranones and Hydroxyridinones: Novel Bidentate Liganda for Cell–Labeling", *J. Med. Chem.*, 1996, 39, 3659–3670.

*Primary Examiner*—Patricia L. Morris
(74) *Attorney, Agent, or Firm*—Nixon & Vanderhye P.C.

(57) ABSTRACT

The present invention relates to a novel process for the preparation of 3-hydroxy-N,1,6-trialkyl-4-oxo-1,4-dihydropyridine-2-carboxamide of formula I:

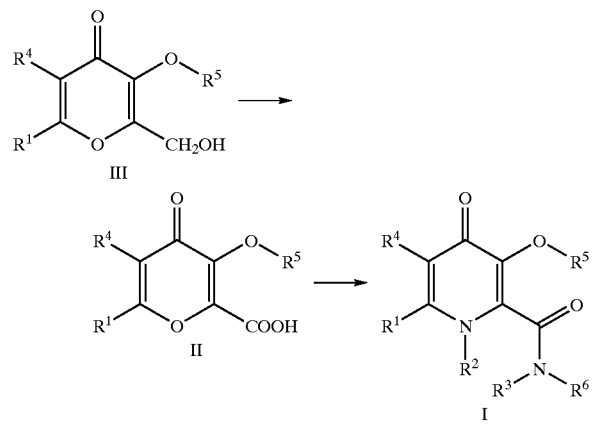

The method comprises of the TEMPO oxidation of a primary alcohol of 3-O-protected-2-hydroxymethyl-6-alkyl-4H-pyran-4-one of formula III to 3-O-protected-4-alkyl-4-oxo-4H-pyran-2-carboxylic acid of formula II. Reaction of compound of formula II with methylamine and 1,1-carbonyidiimidazole in an inert solvent affords 3-O-protected-N,1,6-trialkyl-4-oxo-1,4-dihydropyridine-2-carboxamide, which is deprotected to give of 3-hydroxy-N,1,6-trialkyl-4-oxo-1,4-dihydropyridine-2-carboxamide of formula I.

3 Claims, No Drawings

PROCESSES FOR THE MANUFACTURING OF 3-HYDROXY-N,1,6-TRIALKYL-4-OXO-1,4-DIHYDROPYRIDINE-2-CARBOXAMIDE

This application is a division of Application No. 9/985,269, filed Nov. 2, 2001, the entire content of which is hereby incorporated by reference in this application.

FIELD OF INVENTION

This invention relates to the novel process for the manufacturing of 3-hydroxy-N,1,6-trialkyl-4-oxo-1,4-dihydropyridine-2-carboxamide of formula I,

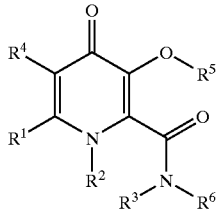

I intermediates of formulae II and III useful in the manufacturing of such 4-oxo-1,4-dihydropyridine-2-carboxamide, and novel process for the manufacturing of the intermediates used.

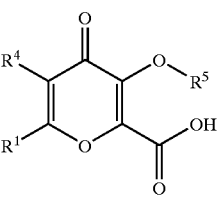

II

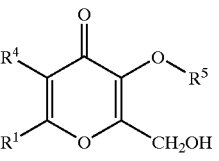

III wherein:

$R^1$, $R^2$, $R^3$, $R^6$ are independently, hydrogen, lower alkyl, $R^4$ is lower alkyl, hydrogen, lower alkoxy, $R^5$ is hydrogen, an alcohol protective group, benzyl and a benzyl group optionally substituted with nitro, lower alkyl and lower alkoxy.

Lower alkyl groups include straight and branched chain hydrocarbon radicals from 1 to 6 carbon atoms.

Lower alkoxy groups include -O-[lower alkyl] wherein lower alkyl is defined above.

Alcohol protective group commonly used includes those which are well known in the art, for example, benzyl, 2,6-dimethylbenzyl, 4-methoxybenzyl, o-nitrobenzyl, 2,6-dichlorobenzyl, 3,4-dichlorobenzyl, 4-(dimethylamino)carbonylbenzyl, 4-methylsulfinylbenzyl, 9-anthrylmethyl, 4-picolyl, heptafluoro-p-tolyl, tetrafluoro-4-pyridyl, formate, acetate, benzoate, benzyloxycarbonyl, methoxycarbonyl, t-butyloxycarbonyl, 2,2,2-trichloroethoxycarbonyl, methoxymethyl, benzyloxymethyl, methoxyethoxymethyl, t-butyl.

According to further aspects of this invention, there are provided methods for the conversion compounds of formula II to 3-benzyloxy-N,1,6-trimethyl-4-oxo-1,4-dihydropyridine-2-carboxamide, and 3-benzyloxy-N,1,6-trialkyl-4-oxo-1,4-dihydropyridine-2-carboxamide, 3-hydroxy-N,1,6-trimethyl-4-oxo-1,4-dihydropyridine-2-carboxamide and 3-hydroxy-N,1,6-trialkyl-4-oxo-1,4-dihydropyridine-2-carboxamide of formula I.

A third aspect of this invention relates to a process of reacting an acid of formula II with 1,1'-carbonyldiimidazole, alkylamine and an inert solvent to give a compound of formula I.

A fourth aspect of this invention concerns the process of oxidizing a compound of formula III with TEMPO, sodium hypochlorite solution, sodium bicarbonate (baking soda) and potassium bromide to give a compound of formula II.

BACKGROUND OF INVENTION

This invention relates to certain 3-hydroxy-N,1,6-trialkyl-4-oxo-1,4-dihydropyridine-2-carboxamide of formula I as orally active iron chelators. Members of the 3-hydroxy-4-oxo-1,4-dihydropyridine class are well known for their ability to chelate iron in physiological environment and these have been reported as useful in the treating iron related disorders such as thalassaemia and anemia, see U.S. Pat. No. 4,840,958, U.S. Pat. No. 5,480,894, U.S. Pat. No. 5,688,815, J. Med. Chem. 1999, 42(23), 4818–4823.

3-Hydroxy-N,1,6-trialkyl-4-oxo-1,4-dihydropyridine-2-carboxamide are bidentate iron I chelators with potential for oral administration, see Bioorganic & Medicinal Chemistry 9 (2001), 563–567. A patent application has been published emphasizing the pharmacological properties of this class of compound, see WO98/54318. Compounds of formula I have been tested in iron mobilization efficacy assay in rat via the mode of oral administration. The results are reported in Table 3 of WO98/54318. Compounds of formula I are chelators possessing high $pFe^{3+}$ values and show great promise in their ability to remove iron under in-vivo conditions.

3-Hydroxy-N,1,6-trimethyl-4-oxo-1,4-dihydropyridine-2-carboxamide has been prepared by the method, described in examples 45 to 48, 53, and 58 of WO98/54318. Allomaltol (1) is converted to 2-(1-hydroxymethyl)-6-methylpyromeconic acid (2) according to the procedure described in FR1516463. The 2-(1-hydroxymethyl)-6-methylpyromeconic acid (2) is reacted with benzyl bromide in sodium hydroxide in a 10:1 mixture of methanol and water to give the 2-hydroxymethyl-3-benzyloxy-6-methyl-pyran-4(1H)-one (3) which is then oxidized with diemthyl sulfoxide and sulfur trioxide.pyridine complex to give 2-formyl-3-benzyloxy-6-methyl-pyran-4(1H)-one (4). Oxidation of the 2-formyl derivative with sulfamic acid and sodium hypochlorite in acetone and water affords 2-carboxyl-3-benzyloxy-6-methyl-pyran4(1H)-one (5). The 2-carboxyl derivative is reacted with dicyclohexyldiimide and 2-mercaptothiazoline and 4-dimethylaminopyridine to give the 3-(2-carbonyl-3-benzyloxy-6-methyl-4(1H)-pyran-2-yl)-1,3-thiazolidine-2-thione (6) which is reacted with methylamine in tetrahydrofuran to give 3-benzyloxy-6-methyl-4(1H)-pyran-2-yl)-2-carboxy-(N-methyl)-amide (7). The 3-benzyloxy-6-methyl-4(1H)-pyran-2-yl)-2-carboxy-(N-methyl)-amide (7) is converted to 1,6-dimethyl-3-benzyloxy4(1H)-pyridinone-2-carboxy-)N-methyl)-amide (8) with methylamine in alcohol. The 3-benzyloxy derivative was deprotected with hydrogenation using Pd/C in dimethylformamide as illustrated in Scheme 1 to give 1,6-dimethyl-3-hydroxy4(1H)-pyridinone-2-carboxy-)N-methyl)-amide (9):

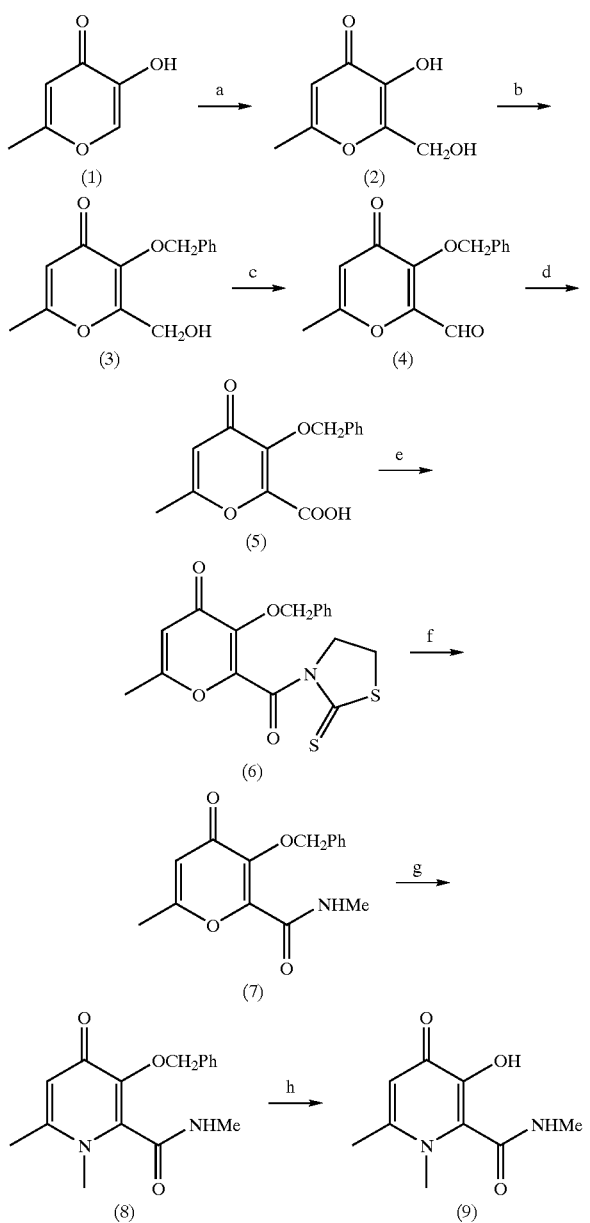

Scheme 1: a. HCHO, NaOH; b. PhCH$_2$Br, NaOH, MeOH, H$_2$O; c. DMSO, SO$_3$.pyridine, CHCl$_3$, Et$_3$N; d. sulfamic acid, NaClO$_2$, acetone, water; e. DCC, CH$_2$Cl$_2$, 2-mercaptothiazoline; f. MeNH$_2$, THF; g. MeNH$_2$, MeOH; h. H$_2$, Pd/C, EtOH.

The IUPAC name of the chemicals shown in Scheme 1 is further clarified below:

Compound (3): 2-hydroxymethyl-3-benzyloxy-6-methyl-pyran4(1H)-one has an alternate IUPAC name 3-(benzyloxy)-2-(hydroxymethyl)-6-methyl-4H-pyran-4-one.

Compound (5): 2-carboxyl-3-benzyloxy-6-methyl-pyran-4(1H)-one has an alternate IUPAC name 3-(benzyloxy)-6-methyl-4-oxo-4H-pyran-2-carboxylic acid.

Compound (8): 1,6-dimethyl-3-benzyloxy4(1H)-pyridinone-2-carboxy-)N-methyl)-amide has an alternate IUPAC name: 3-(benzyloxy)-N,1,6-trimethyl-4-oxo-1,4-dihydropyridine-2-carboxamide.

Compound (9): 1,6-dimethyl-3-hydroxy4(1H)-pyridinone-2-carboxy-)N-methyl)-amide has an alternate IUPAC Name: 3-hydroxy-N,1,6-trimethyl-4-oxo-1,4-dihydropyridine-2-carboxamide.

When compared to the above process, the applicant's invention introduces a number of advantages over the existing process:

1. It affords 1,6-dimethyl-3-benzyloxy-4(1H)-pyridinone-2-carboxy-)N-methyl)-amide in considerably higher yields than existing procedures.

2. It is amenable to industrial scale production since 3-hydroxy-6-methyl-4(1H)-pyran-2-yl)-2-carboxy-(N-methyl)-amide can be made in less process steps from economically, commercially available reagents.

3. It avoids the use of oxidizing agent such as DMSO, sulfur trioxide.pyridine and the need for column chromatography using diethyl ether and the isolation of the intermediate 2-formyl-3-benzyloxy-6-methyl-pyran-4(1H)-one. It avoids the generation of large amount of industrial waste and the execution of the synthesis in two distinct separate steps for the conversion of 2-hydroxymethyl-3-benzyloxy-6-methyl-pyran-4(1H)-one to 3-benzyloxy-2-carboxy-6-methyl-pyran-4(1H)-one. The conversion of 2-hydroxymethyl-3-benzyloxy-6-methyl-pyran-4(1H)-one to 3-benzyloxy-2-carboxy-6-methyl-pyran-4(1H)-one is achieved in one single process step using baking soda (sodium bicarbonate), sodium hypochlorite solution, and TEMPO. The labour cost is significantly reduced because of the short reaction time and ease of work-up.

4. It avoids the isolation and purification of intermediates such as 3-hydroxy-2-hydroxymethyl-6-methyl-pyran-4(1H)-one, 3-benzyloxy-2-formyl-6-methyl-pyran-4(1H)-one, 3-benzyloxy-6-methyl-4(1H)-pyran-2-yl)-2-carboxy-(N-methyl)-amide. The isolation of these intermediates involve extra process step, labour cost, and waste disposal, thereby rendering the process more expensive.

5. It eliminates the use of intermediate 3-(2-carbonyl-3-benzyloxy-6-methyl-4(1H)-pyran-2-yl)-1,3-thiazolidine-2-thione. It does not use 2-mercaptothiazoline which requires its removal as chemical waste in the later step.

6. It avoids the use of reagent dicyclohexyldiimide and the generation of dicyclohexylurea waste that are skin irritant.

7. It does not require three distinct steps for the conversion of 2-carboxyl-3-benzyloxy-6-methyl-pyran-4(1H)-one to 3-benzyloxy-N,1,6-trialkyl-4-oxo-1,4-dihydropyridine-2-carboxamide. The conversion is achieved in one single process step. The labour cost is significantly reduced because of the short reaction time and ease of work-up.

8. An efficient process is described for the large scale manufacturing of 2-chlorokojic acid, a key intermediate for the synthesis of allomaltol. The existing literature process is not amenable to large scale synthesis.

Therefore, one object of the invention is to provide novel process for the production of 1,6-dimethyl-3-benzyloxy-4(1H)-pyridinone-2-carboxy-)N-methyl)-amide and 1,6-dimethyl-3-hydroxy-4(1H)-pyridinone-2-carboxy-)N-methyl)-amide from readily available, inexpensive and relatively safe starting material. Other objects of this invention can be recognized by those skills in the art from the summary of invention and detailed description of embodiments thereof.

SUMMARY OF INVENTION

Scheme 2

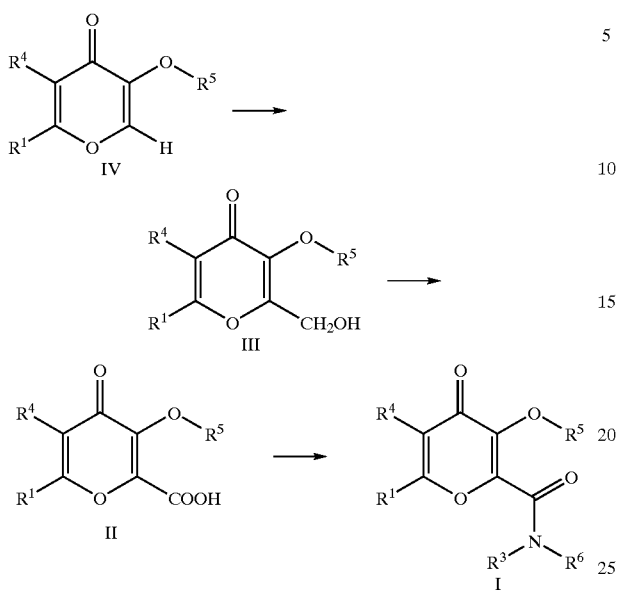

According to one aspect of the invention, a process is provided to make the compound of formula I which comprises of the step of oxidation of III to the acid of formula II in a single process step as shown in scheme 2. The oxidants are TEMPO, baking soda, sodium hypochlorite and potassium bromide. Compound II is then reacted with 1,1'-carbonyldiimidazole and methylamine in an inert solvent to give a compound of formula I in a single process step. The alcohol protective group $R^5$ can be deprotected to give a compound of formula I wherein $R^5$ is hydrogen. The compound of formula III is in turn prepared from the compound of formula IV in a single process step.

DETAILED DESCRIPTION OF INVENTION

Allomaltol (compound of formula IV wherein $R^1$=Me, $R^4$=H, $R^5$=H) is reacted with formaldehyde in a sodium hydroxide solution in methanol and water for a period of 6 to 16 hrs. Benzyl chloride was added and the reaction was heated to reflux for 4 to 12 hours, preferably 6 hours. The benzylated alcohol (compound of formula III wherein $R^1$=Me, $R^4$=H, $R^5$=CH$_2$Ph) is isolated by traditional means. This procedure eliminates the use of a more expensive reagent benzyl bromide and the need to isolate the diol intermediate 3-hydroxy-2-hydroxymethyl-6-methyl-pyran-4(1H)-one. The preparation is achieved in one manufacturing process step. The amount of methanol is critical for the success of the experiment, the preferred amount of solvent mixture is methanol and water in the ratio of 3:2.

The alcohol III is then oxidized to the acid (compound of formula If wherein $R^1$=Me, $R^4$=H, $R^5$=CH$_2$Ph) in a single process step. Jones reagent (chromium trioxide in sulfuric acid) converts the compound III to acid II in acetone, but the yield is extremely low and is less than 10%. A large amount of chromium waste is created. However, TEMPO, sodium hypochlorite, baking soda and potassium bromide affords the acid in very good yield, without chromatography and further recrystallization. The reaction is carried out in an ice bath, with the internal reaction temperature of less than 10° C. The reagents are extremely cheap and the reaction time is less than 24 hours. TEMPO is used in catalytic amount.

The acid II is converted to the amide I in one single process step. The acid is reacted with 1,1'-carbonyldiimidazole in an inert solvent over a period of several hours. A solution of methylamine in alcohol is added. Elevation of the reaction temperature to between 60 to 100° C., preferably 70 to 80° C. for a few hours, affords the amide (compound of formula I wherein $R^1$=Me, $R^2$=Me, $R^3$=Me, $R^6$=H, $R^4$=H, $R^5$=CH$_2$Ph) in a single manufacturing step. The 3-benzyl alcohol protective group (compound of formula I wherein $R^5$=CH$_2$Ph) can be removed by hydrogenation reaction or by acid. Procedures for the removal of protective group can be found in Greene, T. W., in Protective Groups in Organic Synthesis, John Wiley & Sons, 1981.

The starting materials required in this process are commercially available in kilogram to metric ton quantities. Allomaltol is prepared from the zinc reduction of 2-chlorokojic acid. The literature reported the use of excess thionyl chloride for the preparation of 2-chlorokojic acid. The reaction is heterogeneous and the procedure is not amenable to large scale synthesis and manufacture. However, 2-chlorokojic acid can be prepared from kojic acid using 1 to 1.2 equivalent thionyl chloride in an inert solvent. The preferred inert solvent is acetonitrile and the product is easily isolated by filtration.

The above description details a general method for the conversion of compound III to II then to compound I.

The present invention will be more fully understood by the following examples which illustrate the invention, but are not considered limiting to the scope of the invention.

EXAMPLE 1

Preparation of Chlorokojic Acid

A 2-liter 3-neck round bottom flask was equipped with a mechanical stirrer. The flask was charged with kojic acid (0.25 kg, 1.759 mol) and 750 ml acetonitrile at 0° C. The kojic acid was insoluble in acetonitrile and stayed as a suspension. Thionyl chloride (140 ml, 1.919 mol) was added dropwise via a dropping funnel at ice bath temperature. The solid slowly dissolved to give a red clear solution. After 15 minutes, a white solid appeared. After 3 hrs at 0° C., the insoluble solid was filtered. The solid was filtered by suction filtration. The solid was mixed with water (0.5L) and then filtered. The acetonitrile mother liquor was reduced to 15% of the original volume and filtered. The solid was washed with water (200 ml) and then acetonitrile (50 ml). The combined solid was dried to constant weight (269 g, 95.2% yield). M.p. 166–1680° C. [lit value 166–167° C.]. 1H-NMR (DMSO-d$_6$) δ: 4.66 (s, 2H, CH2Cl), 6.57 (s, 1H, CH), 8.12 (s, 1H, CH), 9.3 (br. s, 1H, OH).

EXAMPLE 2

Preparation of 3-(Benzyloxy)-2-(hydroxymethyl)-6-methyl-4H-pyran-4-one

Procedure I

Allomaltol (Chem Abstract 1968-51-OP) was prepared from chlorokojic acid according to literature procedure published in J. Med. Chem., 1996, 39, 3659–3670. Allomaltol (12.6g, 0.1 mol) was added to a solution of sodium hydroxide (4.4 g, 0.11 mol) in water (60 ml). Formaldehyde (9 ml, 37% solution, 0.111 mol) was added dropwise at 0° C. The mixture was stirred at room temperature. A solid started to appear after 1.5 hr. Methanol (50 ml) was added and the mixture was left stirring for 16 hrs. The mixture was heated to 40° C. to effect dissolution of all insoluble solids. Benzyl chloride (12.65 ml, 0.109 mol), tetra-N-butylammonium chloride (71 mg, 0.25 mmol) was added. The mixture was heated to reflux for 3.5 hr. The solution was cooled and the pH of the solution dropped to pH=1. A solution of sodium hydroxide (2.5 g, 0.0625 mol) in water (10 ml) was added. PhCH$_2$Cl (2 ml, 0.0173 mol) was added. The mixture was heated to reflux for 1.5 hr. The pH of the solution was at pH 12.5. The solution was cooled to room temperature. Methanol was removed by evaporation under reduced pressure. The mixture was cooled to 0° C. and extracted with dichloromethane (3×100 ml). The dichloromethane layer was washed with brine, dried over sodium sulfate and evaporated to give a red oil. The oil was mixed with ethyl acetate (250 ml) and heated to effect dissolution. The solution was cooled slowly with stirring to room temperature. A solid appeared. The mixture was cooled in an ice bath for one hr. The solid was isolated by filtration and dried to constant weight (14.5 gm). The mother liquor was evaporated to 15% of the original volume. A solid was formed upon cooling to room temperature and then 0° C. Suction filtration gave an additional 1.7 gm of the titled compound. The total amount of solid isolated was 15.86 g (64.45% yield). H-NMR (CDCl$_3$)δ: 4.31 (s, 2H, CH$_2$OH), 5.21 (s, 2H, CH$_2$Ph), 6.21 (s, 1H, CH), 7.38 (br. s, 5H, Ph). M.p. 115–116° C. (lit. 114–116° C.).

EXAMPLE 3

Preparation of 3-(Benzyloxy)-6-methyl-4oxo-4H-pyran-2arboxylic acid

Procedure I

A 1-liter 3-neck round bottom flask was equipped with a mechanical stirrer and a dropping funnel. Dichloromethane (100 ml) was added to the flask followed by 3-(benzyloxy)-2-(hydroxymethyl)-6-methyl-4H-pyran-4-one (15.87 g, 0.064 mol). Sodium bicarbonate solution (10%, 100 ml, 0.12 mol) was added, followed by solid sodium bicarbonate (13.5 g, 0.161 mol) and potassium bromide (764 mg, 6.42 mmol). The mixture was cooled in an ice bath. The internal temperature of the reaction mixture was 3° C.

TEMPO (100 mg, 0.64 mmol) and tetra-n-butylammonium chloride hydrate (750 mg, 2.7 mmol) were added. Sodium hypochlorite solution (14.6%, 23 ml, 0.045 mol, see note 3) was added dropwise, maintaining the reaction temperature below 7° C. The addition of sodium hypochiorite solution (14.6%, 23 ml, 0.045 mol) took 25 minutes.[1] The pH of the top layer was checked and measured a value of 9.0.

Sodium hypochlorite solution (14.6%, 25 ml, 0.049 mol) was added dropwise[1] over a period of 60 minutes, maintaining the reaction temperature below 7° C. Sodium bicarbonate solution (10%, 50 ml, 0.06 mol) was then added and the pH of the solution was measured after 15 minutes. At this time, the reaction mixture was white in color. The pH of the top layer was checked and had a value of pH 6.4.

Sodium hypochlorite solution (14.6%, 19 ml, 0.037 mol) was added dropwise over 20 min, the pH of the upper layer was now at pH 7.4.2 Sodium bicarbonate (13.5 g, 0.161 mol), TEMPO (60 mg, 0.384 mmol), KBr (700 mg, 5.88 mmol) was added, followed by dichloromethane (20 ml). Sodium hypochlorite (14.6%, 11.5 ml, 0.022 mol) was added dropwise over one hr, maintaining the reaction temperature below 7° C. TLC (EtOAc:hexane) showed that only a small amount of 3-(benzyloxy)-6-methyl-4-oxo-4H-pyran-2-carbaldehyde was present. The reaction mixture was filtered under suction. The filtrate was transferred to a separatory funnel and the lower layer was returned to the reaction vessel.

The upper layer was transferred to a round bottom flask and mixed with 1 gm of sodium thiosulfate to destroy residual sodium hypochlorite. The solution was evaporated under reduced pressure for 5 minutes to remove residual solvent. The solution was cooled in an ice bath and stirred. Concentrated hydrochloric acid was added dropwise until the solution reached pH 1. A white precipitate appeared and was filtered after 1 hr at 0° C. The wet mass weighed 24 g.

The reaction vessel with the dichloromethane layer was mixed with sodium bicarbonate solution (10%, 50 ml, 0.059 mol), sodium bicarbonate (13.5 g, 0.161 mol), potassium bromide (700 mg, 5.88 mmol), tert-n-butylammonium chloride hydrate (500 mg, 1.8 mmol) and mechanically stirred. Sodium hypochlorite solution (14.6%, 14 ml, 0.0274 mol) was added dropwise over a period of 1 hr. The mixture was stirred for an additional 10 minutes and then the two layers were separated. The upper layer was treated with sodium thiosulfate (1 gm) and then stirred. Concentrated hydrochloric acid was added dropwise until the solution reached pH 1. A white precipitate appeared and was filtered after 1 hr at 0° C. The wet mass weighed 2 g.

The combined solid was washed with water and dried to constant weight (15.223 g, 91.1% yield). H-NMR (DMSO-d$_6$) δ:2.30 (s, 3H, Me), 5.10 (s, 2H, PhCH$_2$), 7.35 (m, 2H, Ph), 7.43 (m, 2H, Ph). Mass spec: 261 (M+1). M.p. 173–174° C. [decomposition] (lit 173–175° C.).

Note[1]: The solution turned yellow upon addition of the sodium hypochlorite. Addition was stopped until the mixture turned white in color. The addition of sodium hypochlorite was resumed and to maintain the yellow color.
Note[2]: The pH of the reaction was measured with a pH meter.
Note[3]: Sodium hypochlorite solution was titrated before use. The following procedure is representative:

Sodium thiosulfate pentahydrate (12.405 g) was dissolved in water in a 250 ml volumetric flask. The solution was diluted to 2.50 ml. Potassium iodide (3 g) was suspended in 100 ml acetic acid in a 250 ml flask and stirred for 30 min at room temperature. The test sodium hypochlorite solution (2 ml) was pipetted into this mixture. A brown color was formed immediately and the mixture was titrated against 0.2M sodium thiosulfate solution from a buret until the solution turned colorless. The amount of solution required to the end point is Vs.

Therefore $0.5*0.2M*Vs=M_{NaOCl}*2$ ml:

The molarity of the sodium hypochlorite solution $M_{NaOCl}$ was calculated.

Procedure II

A 500 ml round bottom flask was equipped with a stirrer and a dropping funnel. Dichloromethane (15 ml) was added to the flask followed by 3-(benzyloxy)-2-(hydroxymethyl)-6-methyl-4H-pyran-4-one (3 g, 0.01233 mol). Sodium bicarbonate (2.6 g, 0.031 mol) and potassium bromide (146 mg, 0.001233 mol) and water (5 ml) was added. The mixture was cooled in an ice bath. The internal temperature of the reaction mixture was 3° C.

TEMPO (19.26 mg, 0.123 mmol) and tetra-n-butylammonium chloride hydrate (140.5 mg, 0.615 mmol) were added. Sodium hypochlorite solution (4.7%, 25 ml, 0.0158 mol) was added dropwise, maintaining the reaction temperature below 7° C. The addition took 30 minutes. The pH of the solution dropped to 6.4. Sodium bicarbonate (4.3 g, 0.0512 mol) was added. The pH rose to 7.5.

Sodium hypochlorite solution (4.7%, 23 ml, 0.0145 mol) was added dropwise over a period of 20 minutes, maintaining the reaction temperature below 7° C. One drop of the solution was removed and tested with a test tube containing potassium iodide (20 mg) in acetic acid (2 ml). The solution turned yellow. This showed that very little excess of sodium hypochlorite was present.

At 2.5 hr since the start of the experiment, the two phases were separated. The aqueous phase mixed with sodium thiosulfate (1 g) in water (2 ml). The solution was evaporated for 5 minutes to remove residual organic solvent and then acidified to pH 1 with stirring at 0° C. with dropwise addition of concentrated HCl. A white precipitate appeared and was filtered after cooling at 0° C. for 1 hr. The white solid was washed with water and then dried to constant weight (2.76 g, 87% yield).

Procedure III

A 1-liter 3-neck round bottom flask was equipped with a mechanical stirrer and a dropping funnel. Dichloromethane (300 ml) was added to the flask followed by 3-(benzyloxy)-2-(hydroxymethyl)-6-methyl-4H-pyran-4-one (63.48 g, 0.2574 mol). Sodium bicarbonate solution (10%, 200 ml, 0.24 mol) was added, followed by solid sodium bicarbonate (54 g, 0.6428 mol) and potassium bromide (3.06 g, 0.02574 mol). The mixture was cooled in an ice bath. The internal temperature of the reaction mixture was 3° C. TEMPO (400 mg, 0.00256 mol) and tetra-n-butylammonium chloride hydrate (2.98 g, 0.01287 mol) were added. Sodium hypochlorite solution (14.6%, 250 ml, 0.49 mol) was added dropwise, maintaining the reaction temperature below 7° C. The addition of sodium hypochlorite solution took 35 minutes. The pH of the top layer was checked and measured a value of 8.0. Solid sodium bicarbonate (27 g, 0.321 mol) was added, followed by the dropwise addition of sodium hypochlorite solution (14.6%, 100 ml, 0.195 mol) over a period of 50 minutes at ice bath temperature. Solid sodium bicarbonate (20 g, 0.238 mol), 10% sodium bicarbonate solution (100 ml, 0.119 mol), potassium bromide (3 g, 0.0252 mol), and tetra-n-butylammonium chloride hydrate (2 g, 0.0087 mol) was added. Sodium hypochlorite solution (14.6%, 85 ml, 0.167 mol) was added dropwise over a period of two hrs. The pH of the solution dropped to 6.0. Solid sodium bicarbonate (16 g, 0.190 mol) and potassium bromide (3 g, 0.025 mol) were added, followed by the dropwise addition of sodium hypochlorite solution (14.6%, 50 ml, 0.098 mol) over 10 minutes. After 30 minutes of stirring at ice bath temperature, the reaction mixture was filtered under suction. The filtrate was transferred to a separatory funnel. The upper layer was transferred to a round bottom flask and mixed with 1 gm of sodium thiosulfate to destroy residual sodium hypochlorite. The solution was evaporated under reduced pressure for 5 minute to remove residual solvent. The solution was cooled in an ice bath and stirred. Concentrated hydrochloric acid was added dropwise until the solution reached pH 1. A white precipitate appeared and was filtered after 1 hr at 0° C. The solid was washed with water and dried to constant weight (49.04 g, 73% yield).

Procedure IV

A 250 ml round bottom flask was equipped with a stirrer and a dropping funnel. Dichloromethane (5 ml) was added to the flask followed by 3-(benzyloxy)-2-(hydroxymethyl)-6-methyl-4H-pyran-4-one (1 g, 4.06 mmol). Sodium bicarbonate (314 mg, 3.74 mol) and potassium bromide (96.5 mg, 0.81 mmol) in water (2.5 ml) were added. The mixture was cooled in an ice bath. The internal temperature of the reaction mixture was 3° C.

TEMPO (6.4 mg, 0.041 mmol) was added. Sodium hypochlorite solution (4.7%, 7.5 ml, 4.73 mmol) was added dropwise, maintaining the reaction temperature below 7° C. After 1.5 hr, TLC (EtOAc/hexane) showed all the starting material has been converted to the 3-(benzyloxy)-6-methyl-4-oxo-4H-pyran-2-carbaldehyde. At this time, the mixture was red in color. An additional amount of sodium hypochlorite solution (4.7%, 6.5 ml, 4.1 mmol) was added dropwise at ice bath temperature. The mixture was stirred at ice bath temperature for 1 hr. The two layers were separated. The aqueous layer was tested for excess hypochiorite. One drop of the solution was mixed with KI (20 mg) in acetic acid (2 ml). The solution turned yellow indicating that there was very little sodium hypochlorite left. The aqueous layer was evaporated under reduced pressure for 3 minutes to remove organic solvent. It was cooled in an ice bath and rapidly stirred. Conc. HCl was added until the pH reached 1. An insoluble white solid appeared and was isolated by suction filtration. The material was washed with water and dried to constant weight (800 mg). The dichloromethane layer from the extraction was mixed a suspension of potassium bromide (84 mg, 0.71 mmol) and sodium bicarbonate (180 mg, 2.14 mmol) in water (3 ml) at ice bath temperature. Sodium hypochlorite (4.7%, 3 ml, 1.89 mmol) was added dropwise. After 1 hr, the two layers were separated, the aqueous phase was extracted with dichloromethane (5 ml), and then evaporated to remove residual organic solvent. The aqueous phase was acidified to pH 1 by the dropwise addition of conc. HCl at ice bath temperature. The insoluble white solid was filtered and dried to constant weight (203 mg). The combined product (1.003 g) was isolated in 98.9% yield.

EXAMPLE 4

Preparation of 3-(Benzyloxy)-N,1,6-trimethyl-4oxo-1,4-dihydropyridine-2-carboxamide Procedure I 1,1'-carbonyldiimidazole (3.2 g, 19.7 mmol) was added to a solution of the 3-(benzyloxy)-6-methyl-4-oxo-4H-pyran-2-carboxylic acid (3.2 g, 12.3 mmol) in DMF (25 ml) at room temperature. The resulting solution was heated at 45 to 50° C. for 3 hrs. A clear yellow solution was observed. A solution of methylamine in methanol (25 ml of 1M solution, 27.33 mmol) was added. The reaction mixture was stirred at 65 to 70° C. for 3 hr under pressure in a sealed system. The reaction was cooled between 40 to 50° C. at which time a solution of methylamine in methanol (20 ml of 1M solution, 21.87 mmol) was added. The solution was stirred at 65 to 70° C. for 15 hrs under pressure. The solvent was removed under reduced pressure and dichloromethane was added (150 ml). The solution was washed with water and dried over magnesium sulfate (2 g). Solvent evaporation gave a yellow oil that was passed through a short silica gel column (3" height by 1" diameter). The column was eluted with 10% methanol in ethyl acetate to give the titled compound (2.3 g, yield 66%). H-NMR (CDCl$_3$) δ:2.20 (s, 3H, Me), 2.68 (d, 3H, NHMe), 3.49 (s, 3H, NMe), 5.03 (s, 2H, PhCH$_2$), 6.14 (s, 1H, CH), 7.32 (m, 5H, Ph), 0.788 (br. s, 1H, NH). H-NMR (DMSO-d$_6$):2.28 (s,3H, Me), 2.74 (d, 3H, NHMe), 3.42 (s, 3H, NMe), 5.05 (s, 2H, PhCH$_2$), 6.20 (s, 1H, CH), 7.33 (m, 5H, Ph), 0.8.77 (br. s, 1H, NH). Mass spect. 287 (M+1). M.p. 187.5–188.5° C. (lit m.p. 164–165.5° C.: source p. 35, WO98/54138).

Procedure II 1,1'-carbonyldiimidazole (0.5 g, 3.07 mmol) was added to a solution of the 3-(benzyloxy)-6-methyl-4-oxo-4H-pyran-2-carboxylic acid (0.5 g, 1.92 mmol) in DMF (25 ml) at room temperature. The resulting solution was heated at 45 to 50° C. for 2.5 hrs. A clear yellow solution was observed. A solution of methylamine in methanol (5 ml of 2M solution, 0.01 mol) was added. The reaction mixture was stirred at 45 to 50° C. for 2.5 hrs, and then stirred at room temperature for 15 hrs. A solution of methylamine in methanol (5 ml of 2M solution, 0.01 mol). The solution was stirred at 65 to 70° C. for 2 hrs in a sealed tube. The solvent was removed under reduced pressure and dichloromethane was added (50 ml). The solution was washed with water and dried over magnesium sulfate. Solvent evaporation gave a yellow oil, which was passed through a short silica gel column (3" height by 1" diameter). The column was eluted with 10% methanol in ethyl acetate to give the titled compound (0.27 g, yield 72%).

EXAMPLE 5

Preparation of 3-(Benzyloxy)-N,N-diethyl-1,6-dimethyl-4-oxo-1,4-dihydropyridine-2-carboxamide 1,1'-carbonyldiimidazole (1.87 g, 111.53 mmol) was added to a solution of the 3-(benzyloxy)-6-methyl-4-oxo-4H-pyran-2-carboxylic acid (2.0 g, 7.69 mmol) in DMF (15 ml) at room temperature. The resulting solution was heated at 40° C. for 3 hrs. A clear yellow solution was observed. Diethylamine (1.08 ml, 9.2 mmol) was added. The reaction mixture was stirred at 40 to 45° C. for 2 hrs. The reaction was cooled to room temperature at which time a solution of methylamine in methanol (11 ml of 2M solution in methanol, 15.4 mmol) was added. The solution was stirred at 65 to 70° C. for 15 hrs under pressure. The solvent was removed under reduced pressure and dichloromethane was added (70 ml). The solution was washed with water and dried over magnesium sulfate (1 g). Solvent evaporation gave light yellow oil as a crude product. The column was eluted with 10% to 25% methanol in ethyl acetate to give the titled compound (1.74 g, yield 67%). H-NMR (CDCl$_3$) σ:1.09 (t, J=7.11 Hz, 3H, Me), 1.16 (t, J=7.04 Hz 3H, Me), 2.34 (s, 3H, Me), 3.13–3.30 (m, 2H, CH$_2$), 3.47 (s, 3H, NMe), 3.50–3.60 (m, 2H, CH$_2$), 4.91(d, J=10.76 Hz, 1H, CH$_2$), 5.52(d, J=10.74 Hz, 1H, CH$_2$), 6.41 (s, 1H, CH), 7.10–7.33 (m, 5H, Ph), Mass spect. 329 (M+1).

EXAMPLE 6

Preparation of N,N-diethyl-3-hydroxy-1,6-dimethyl-4-oxo-1,4-dihydropyridine-2-carboxamide Pd(OH)$_2$ on charcoal (0.1 g) was added to a solution of 3-(benzyloxy)-N,N-diethyl-1,6-dimethyl-4-oxo-1,4-dihydropyridine-2-carboxamide(1.0 g, 3.05 mmol) in ethanol (100 ml) under nitrogen. The mixture was hydrogenated at 50 psi hydrogen for 4 hrs. The Pd(OH)$_2$ was removed by filtration through Celite and the Celite cake was washed with ethanol (3×10 ml). The ethanol filtrate was evaporated to give a slightly red solid (0.66 g, 94%). Melting point: 128 to 130° C. H-NMR (CDCl$_3$) σ:1.19 (t, J=7.11 Hz, 3H, Me), 1.30 (t, J=7.00 Hz, 3H, Me), 2.36 (s, 3H, Me), 3.36 (m, 2H, CH$_2$), 3.38 (s, 3H, NMe), 3.64 (q, J=6.90 Hz, 2H, CH$_2$), 6.35 (s, 1H, CH), Mass spect. 239 (M+1).

EXAMPLE 7

Preparation of 3-hydroxy-N,1,6-trimethyl-4-oxo-1,4-dihydropyridine-2-carboxamide Pd(OH)$_2$ on charcoal (0.2 g) was added to a solution of 3-(benzyloxy)-N,1,6-trimethyl-4-oxo-1,4-dihydropyridine-2-carboxamide (1.25 g, 4.366 mmol) in ethanol (120 ml) under nitrogen. The mixture was hydrogenated at 50 psi hydrogen for 4 hrs. The Pd(OH)$_2$ was removed by filtration through Celite and the Celite cake was washed with ethanol (3×25 ml). The Celite cake was further stirred with ethanol (100 ml) and then filtered through Celite. The combined ethanol filtrate was evaporated to give a solid (0.86 g, quantitative yield). Melting point: >250° C. H-NMR (COCl$_3$:DMSO-d$_6$ [2:1]) δ:1.81 (s, 3H, Me), 2.34 (d, 3H, NHMe), 3.01 (s, 3H, NMe), 5.67 (s, 1H, CH), 7.88 (s, 1H, NH). Elemental Analysis: Calc. C 55.09; H 6.6; N 14.28. Found. C 54.67; H 6.31; N 14.12.

What is claimed is:

1. A process for the preparation of a compound of formula I:

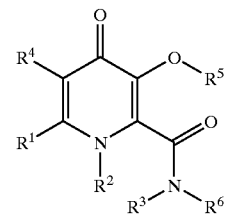

wherein:

$R^1$, $R^2$, $R^3$, $R^6$ are, independently, hydrogen or a lower alkyl, $R^4$ is a lower alkyl, hydrogen, or a lower alkoxy, $R^5$ is hydrogen or an alcohol protective group, comprising:

(i) reacting a compound of formula II:

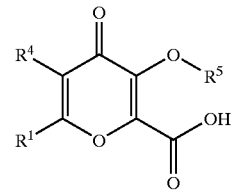

wherein $R^1$, $R^4$, $R^5$ are as defined above, with 1,1'-carbonyldiimnidazole;

(ii) reacting the mixture resulting from step (i) with a compound of formula
$R^3R^6NH$, wherein $R^3$ and $R^6$ are as defined above, and (iii) reacting the mixture resulting from step (ii) with $R^2NH_2$ so that said compound of formula I is produced.

2. The process of claim 1 wherein:

$R^1$, $R^2$ and $R^3$ are methyl, $R^4$ is hydrogen, $R^5$ is benzyl, and $R^6$ is hydrogen.

3. The process of claim 1 wherein said alcohol protective group is benzyl or a benzyl group substituted with nitro, a lower alkyl or a lower alkoxy.

* * * * *